(12) United States Patent
Kim et al.

(10) Patent No.: US 10,710,944 B2
(45) Date of Patent: Jul. 14, 2020

(54) METHOD OF PREPARING BUTADIENE

(71) Applicant: LG CHEM, LTD., Seoul (KR)

(72) Inventors: Eun Kyo Kim, Daejeon (KR); Mi Kyung Kim, Daejeon (KR); Jae Ik Lee, Daejeon (KR); Jeong Seok Lee, Daejeon (KR)

(73) Assignee: LG CHEM, LTD., Seoul (KR)

(*) Notice: Subject to any disclaimer, the term of this patent is extended or adjusted under 35 U.S.C. 154(b) by 0 days.

(21) Appl. No.: 16/072,751

(22) PCT Filed: Dec. 18, 2017

(86) PCT No.: PCT/KR2017/014932
§ 371 (c)(1),
(2) Date: Jul. 25, 2018

(87) PCT Pub. No.: WO2018/124575
PCT Pub. Date: Jul. 5, 2018

(65) Prior Publication Data
US 2019/0031580 A1    Jan. 31, 2019

(30) Foreign Application Priority Data

Dec. 29, 2016 (KR) .......................... 10-2016-0182368

(51) Int. Cl.
*C07C 5/333* (2006.01)
*C07C 7/04* (2006.01)
(Continued)

(52) U.S. Cl.
CPC .............. *C07C 5/3332* (2013.01); *C07C 5/48* (2013.01); *C07C 7/00* (2013.01); *C07C 7/005* (2013.01);
(Continued)

(58) Field of Classification Search
CPC ........... C07C 5/3332; C07C 7/09; C07C 7/12; C07C 7/20; C07C 11/16; C07C 2523/745;
(Continued)

(56) References Cited

U.S. PATENT DOCUMENTS 7,741,173 B2   6/2010  Koyanagi et al.
9,738,574 B2   8/2017  Lee et al.
(Continued)

FOREIGN PATENT DOCUMENTS

JP    2016-503073 A    2/2016
JP    2016-172721 A    9/2016
(Continued)

*Primary Examiner* — Ali Z Fadhel
(74) *Attorney, Agent, or Firm* — Dentons US LLP

(57) ABSTRACT

The present invention relates to a method of preparing butadiene and a device for preparing the same. According to the present invention, since butane is used as a diluent gas, even when a refrigerant belonging to a grade lower than a very low temperature refrigerant is used, a C4 mixture and gas products excluding butadiene may be easily separated, and loss of active ingredients may be minimized, which may increase productivity while reducing raw material costs, thereby improving economic efficiency. In addition to these advantages, when the method and device of the present invention are used, high-purity butadiene may be safely prepared.

14 Claims, 3 Drawing Sheets

(51) Int. Cl.
*C07C 5/48* (2006.01)
*C07C 7/00* (2006.01)
*C07C 7/11* (2006.01)
*C07C 7/09* (2006.01)
*C07C 7/12* (2006.01)
*C07C 7/20* (2006.01)
*C07C 11/16* (2006.01)
*B01D 53/14* (2006.01)

(52) U.S. Cl.
CPC ............... *C07C 7/04* (2013.01); *C07C 7/09* (2013.01); *C07C 7/11* (2013.01); *C07C 7/12* (2013.01); *C07C 7/20* (2013.01); *C07C 11/16* (2013.01); *B01D 53/1487* (2013.01); *C07C 2523/745* (2013.01)

(58) Field of Classification Search
CPC .. C07C 5/48; C07C 7/005; C07C 7/11; C07C 7/00; C07C 7/04; B01D 53/1487
See application file for complete search history.

(56) References Cited

U.S. PATENT DOCUMENTS

| 2007/0244349 A1 | 10/2007 | Crone et al. |
| 2014/0200381 A1 | 7/2014 | Josch et al. |
| 2018/0002254 A1* | 1/2018 | Josch .................. C07C 5/48 |
| 2018/0362419 A1* | 12/2018 | Li ....................... C07C 5/48 |

FOREIGN PATENT DOCUMENTS

| JP | 2017-518992 A | 7/2017 |
| KR | 10-2012-0103759 | 9/2012 |
| KR | 10-1256247 | 4/2013 |
| KR | 10-2015-0139428 | 12/2015 |
| KR | 10-1655557 | 9/2016 |
| WO | 2014/111409 A1 | 7/2014 |
| WO | 2015/051028 A1 | 4/2015 |
| WO | 2016/003215 A1 | 1/2016 |

* cited by examiner

METHOD OF PREPARING BUTADIENE

CROSS-REFERENCE TO RELATED APPLICATION

This application is a National Stage filing under 35 U.S.C. 371 of International Application No. PCT/KR2017/014932 filed on Dec. 18, 2017, and claims priority to Korean Patent Application No. 10-2016-0182368, filed on Dec. 29, 2016 in the Korean Intellectual Property Office, the disclosure of which is incorporated herein by reference.

TECHNICAL FIELD

The present invention relates to a method of preparing butadiene. More specifically, the present invention relates to a method of preparing butadiene, which enables preparation of high-purity butadiene through economically efficient processes capable of increasing productivity by minimizing loss of hydrocarbons including butadiene, and also enables preparation of high-purity butadiene in a safe manner by allowing a vapor phase stream to deviate from an explosive range after hydrocarbons are absorbed.

BACKGROUND ART

Butadiene, an important basic fraction, is used as an intermediary for various petrochemical products, and demand and value thereof are gradually increasing in the petrochemical market.

Butadiene can be extracted from the C4 fraction through naphtha cracking or obtained by direct dehydrogenation or oxidative dehydrogenation of butene.

Thereamong, according to the method of preparing butadiene through oxidative dehydrogenation of butene, oxygen is used as a reactant, and two hydrogens are removed from butene to generate butadiene. In this case, water generated as a result of the reaction is stable. Thus, the method is thermodynamically very advantageous. In addition, since oxidative dehydrogenation is an exothermic reaction unlike direct dehydrogenation, butadiene may be obtained in high yield even at low reaction temperature as compared with direct dehydrogenation. Therefore, using the method of preparing butadiene through oxidative dehydrogenation of butene, it is possible to effectively meet increasing demand for butadiene.

In addition, according to the method of preparing butadiene through oxidative dehydrogenation of butene, in addition to raw materials, nitrogen, steam, or the like is added as a diluent gas for the purpose of reducing explosion risk due to oxygen and for removal of heat of reaction. When hydrocarbons are separated from reaction products including diluent gases, light gas species (COx, $O_2$, and the like), hydrocarbons, and the like, a method of absorbing hydrocarbons from reaction products or a method of liquefying hydrocarbons by cooling reaction products may be used. Thereamong, the absorption method is mainly used. In the case of the liquefaction method, a very low-temperature refrigerant is required for liquefaction due to diluent gases, light gas species, and the like present in reaction products. This increases equipment costs, operating costs, and energy consumption, which may lower economic efficiency of processes. For this reason, the absorption method is preferred.

In this regard, FIG. 1 shows a schematic diagram for explaining a conventional device for preparing butadiene and a conventional method of preparing the same.

Referring to FIG. 1, the conventional device includes an oxidative dehydrogenation reaction part 110 responsible for generating reaction products including butadiene from reaction raw materials including butene, oxygen ($O_2$), steam, and nitrogen as a diluent gas; a cooling separation part 120 responsible for separating water from the reaction products generated through oxidative dehydrogenation; an absorption separation part 130 responsible for separating butadiene or a C4 mixture containing butadiene, and hydrocarbons from the oxidative dehydrogenation reaction products, from which water is separated; and a purification part 140 responsible for purifying butadiene from the butadiene-containing stream separated in the absorption separation part 130.

The oxidative dehydrogenation reaction part 110 may be operated to react reaction raw materials including butene, oxygen ($O_2$), steam, a diluent gas ($N_2$), and unreacted butene recovered in the purification part in the presence of a ferrite catalyst or a bismuth molybdate catalyst under isothermal or adiabatic conditions.

The cooling separation part 120 may be operated by a quenching-type direct cooling system (quencher) or an indirect cooling system.

FIG. 1 shows an example of selectively absorbing and separating only butadiene in the absorption separation part 130. In the absorption separation part 130, only butadiene may be selectively absorbed from reaction products from which water is separated, or all hydrocarbons including a C4 mixture may be absorbed using a solvent. Specific examples of solvents capable of selectively absorbing butadiene may include acetonitrile (ACN), N-methylpyrrolidone (NMP), dimethyl formamide (DMF), and the like, and specific examples of solvents capable of absorbing all hydrocarbons including a C4 mixture may include toluene, xylene, and the like. In the absorption separation part 130, COx, $O_2$, and $N_2$ used as a diluent gas are all incinerated, or in some cases, a portion thereof is recovered in the reaction part and reused, and the remainder is incinerated.

For example, the purification part 140 is conventional butadiene purification equipment. In the purification part 140, an acetonitrile (ACN) process, a N-methylpyrrolidone (NMP) process, or a dimethyl formamide (DMF) process may be performed. When necessary, parts of these processes may be performed in modified form to purify butadiene.

However, in general, an excess of a solvent is used in an absorption separation process. Thus, a large amount of energy is consumed in the process of recovering an absorption solvent and the process of recovering and purifying butadiene in the purification part 140. Alternatively, when the absorption separation process is replaced by a condensation process, a very low-temperature refrigerant is required. In this case, energy consumption, raw material costs, and production costs are increased, thereby lowering economic efficiency of processes. Therefore, there is an urgent need to develop related technologies to solve these problems.

PRIOR ART DOCUMENT

[Patent Document] (Patent Document 1) KR 10-2012-0103759 A

DISCLOSURE

Technical Problem

Therefore, the present invention has been made in view of the above problems, and it is one object of the present invention to provide a method of preparing butadiene. According to the method of the present invention, when butadiene is prepared through oxidative dehydrogenation of butene, unlike conventional methods, in which nitrogen is used as a diluent gas and an absorption method is used to separate butadiene from reaction products, butane is used as a diluent gas and a condensation method, in which butadiene is liquefied and separated from reaction products using a low-temperature refrigerant or cooling water, is used. In particular, to minimize the amount of active ingredients (all hydrocarbons including butadiene) discharged with a stream including COx, $O_2$, n-butane, and the like separated in a condensation separation process, a method of selectively recovering active ingredients from an upper stream generated in the condensation separation process is used.

The above and other objects can be accomplished by the present disclosure described below.

Technical Solution

In accordance with one aspect of the present invention, provided is a method of preparing butadiene, including a step of obtaining oxidative dehydrogenation reaction products containing butadiene, which are generated when reaction raw materials containing butene, oxygen ($O_2$), steam, and a diluent gas are passed through an oxidative dehydrogenation reaction part;

a step of separating water from the oxidative dehydrogenation reaction products containing butadiene by passing the oxidative dehydrogenation reaction products through a cooling separation part;

a step of condensing hydrocarbons by passing the oxidative dehydrogenation reaction products, from which water is separated, through a condensation separation part;

a step, in which oxidative dehydrogenation reaction products containing hydrocarbons not condensed in the condensation separation part are passed through an absorption separation part under the conditions that a noncombustible diluent gas is fed, and a solvent capable of selectively absorbing butadiene is used to separate COx, $O_2$, n-butane, butene, and butadiene, and the separated COx, $O_2$, n-butane, butene, and butadiene are fed again into the condensation separation part; and a step, in which crude hydrocarbons including n-butane, butene, and butadiene, which are condensed in the condensation separation part, are passed through a purification part to separate butadiene, or the crude hydrocarbons are passed through a degasification part to additionally separate COx and $O_2$, and then the crude hydrocarbons are passed through the purification part to separate butadiene, wherein a gas containing n-butane remaining after butadiene is separated in the purification part is fed again into the oxidative dehydrogenation reaction part;

a discharge stream containing butene remaining after butadiene is separated in the purification part is mixed with butene supplied as a raw material and fed into the oxidative dehydrogenation reaction part; and the diluent gas is butane.

In accordance with another aspect of the present invention, provided is a device for preparing butadiene, including an oxidative dehydrogenation reaction part, in which oxidative dehydrogenation of reaction raw materials containing butene, oxygen ($O_2$), steam, and a diluent gas is performed to obtain oxidative dehydrogenation reaction products containing butadiene;

a cooling separation part responsible for separating water from the reaction products resulting from oxidative dehydrogenation;

a condensation separation part responsible for condensing hydrocarbons from the oxidative dehydrogenation reaction products, from which water is separated;

an absorption separation part responsible for separating COx, $O_2$, and a noncombustible diluent gas from oxidative dehydrogenation reaction products containing hydrocarbons not condensed in the condensation separation part under the conditions that a noncombustible diluent gas is fed and a solvent capable of selectively absorbing butadiene is used; and a purification part responsible for separating butadiene from crude hydrocarbons including n-butane, butene, and butadiene, which are condensed in the condensation separation part, wherein hydrocarbons including n-butane, butene, and butadiene, which are selectively absorbed to the solvent in the absorption separation part, are fed again into the condensation separation part;

a gas containing n-butane remaining after butadiene is separated in the purification part is fed again into the oxidative dehydrogenation reaction part;

a discharge stream containing butene remaining after butadiene is separated in the purification part is mixed with butene supplied as a raw material and fed into the oxidative dehydrogenation reaction part; and the diluent gas is butane.

Advantageous Effects

As apparent from the foregoing, the present invention advantageously provides a method of preparing butadiene. According to the present invention, when butadiene is prepared through oxidative dehydrogenation of butene, unlike conventional methods, in which nitrogen is used as a diluent gas and an absorption method is used to separate butadiene from reaction products, butane is used as a diluent gas and a condensation method, in which butadiene is liquefied and separated from reaction products using a low-temperature refrigerant or cooling water, is used. In addition, an absorption method of selectively recovering hydrocarbons from an upper stream generated in a condensation process is used, so that loss of hydrocarbons is minimized. Therefore, the method of the present invention can reduce energy consumption, raw material costs, and production costs, thereby improving economic efficiency of processes. In addition, use of the method of the present invention enables preparation of high-purity butadiene in a safe manner by allowing a vapor phase stream to deviate from an explosive range after hydrocarbons are absorbed.

BEST MODE

Hereinafter, the method of preparing butadiene and the device for preparing the same according to the present invention will be described in detail. According to the present invention, butane is used as a diluent gas when a condensation separation process is performed, and an absorption separation process, in which active ingredients contained in a stream discharged to the outside through the upper portion of a condensation separation part are selectively recovered under the conditions that a noncombustible diluent gas is fed, is employed. In the case that butane is used as a diluent gas as described above, in the condensation separation part, hydrocarbons may be easily separated from oxidative dehydrogenation reaction products using a low-temperature refrigerant or cooling water. In addition, by using a solvent capable of selectively absorbing butadiene under the conditions that a noncombustible diluent gas is fed, hydrocarbons discharged to the outside may be selectively absorbed in the absorption separation part to minimize the amount of active ingredients discharged to the outside of the system. Thus, when the method and device of the present invention are used, butadiene may be stably prepared while reducing production costs and the risk of explosion.

The method of preparing butadiene and the device for preparing the same according to the present invention will be described in detail with reference to the accompanying drawings. FIGS. 2 to 6 include schematic diagrams for explaining the device for preparing butadiene and the method of preparing the same according to the present invention.

Figure 1:
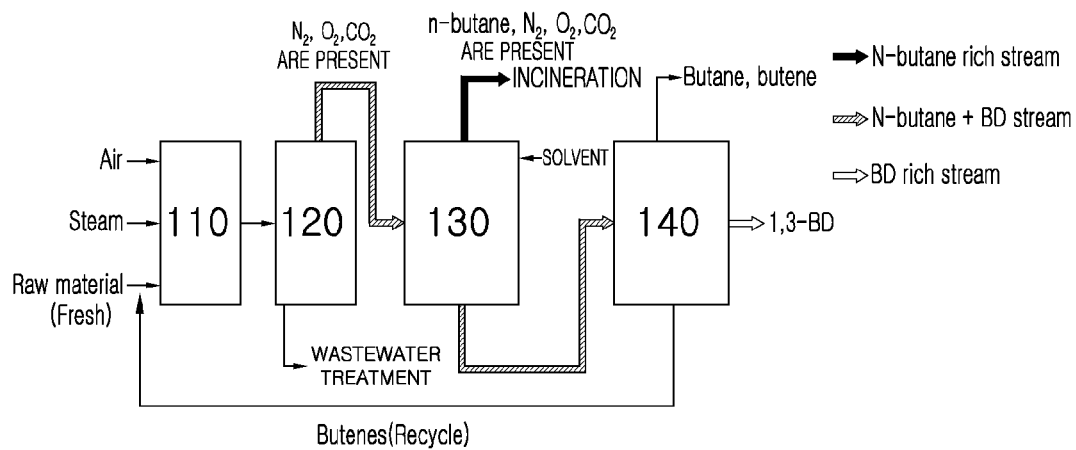
FIG. 1 shows a schematic diagram for explaining a conventional device for preparing butadiene and a conventional method of preparing the same.
Figure 2:
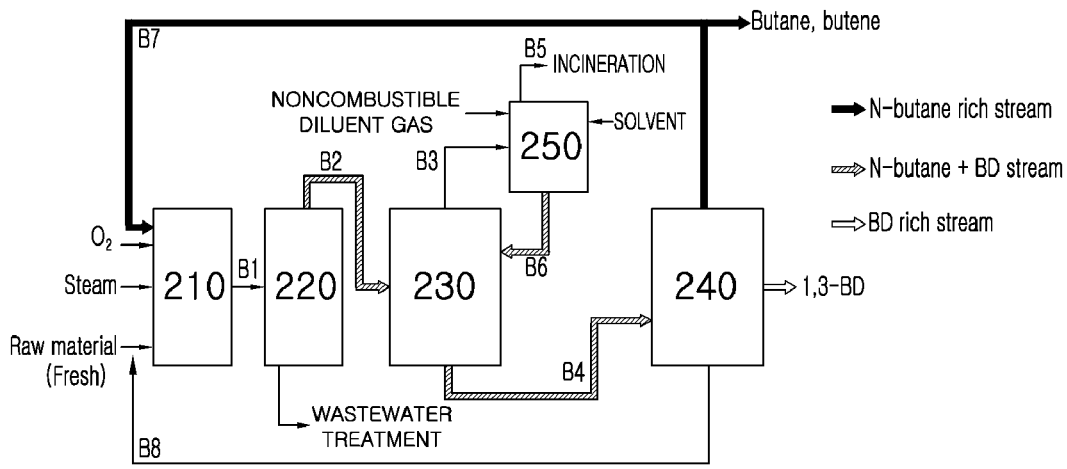
FIGS. 2 to 6 include schematic diagrams for explaining the device for preparing butadiene and the method of preparing the same according to the present invention.

Referring to FIG. 2, first, reaction raw materials containing butene, oxygen ($O_2$), steam, and a diluent gas (butane) are passed through an oxidative dehydrogenation reaction part 210 to obtain oxidative dehydrogenation reaction products containing butadiene. At this time, raw materials for oxidative dehydrogenation may be combined with discharge streams B7 and B8 resulting from a purification process, and introduced into the oxidative dehydrogenation reaction part 210. A stream B1 discharged after the process may contain butadiene, n-butane, butene, $O_2$, COx, $H_2O$, and the like. The stream B1 discharged from the oxidative dehydrogenation reaction part 210 is introduced into a cooling separation part 220, and water is separated therefrom.

A discharge stream B2 generated after the cooling separation process may contain butadiene, n-butane, butene, $O_2$, COx, and the like, and the discharge stream B2 is introduced into a condensation separation part 230.

A discharge stream B3 generated after the condensation separation process may contain oxidative dehydrogenation reaction products containing hydrocarbons not condensed when hydrocarbons are condensed using cooling water through compression/cooling in the condensation separation process. The discharge stream B3 may be introduced into an absorption separation part 250, and hydrocarbons may be recovered from the discharge stream B3 using a solvent capable of selectively absorbing butadiene under the conditions that a noncombustible dilute gas is injected.

For example, the noncombustible dilute gas may be nitrogen gas ($N_2$), argon, helium, or carbon dioxide ($CO_2$), preferably nitrogen gas. In this case, the molar fraction of oxygen ($O_2$) to hydrocarbons such as n-butane is lowered, so that an explosive range may be avoided.

For example, the solvent capable of selectively absorbing butadiene may be acetonitrile (ACN), N-methylpyrrolidone (NMP), or dimethyl formamide (DMF). In this case, butadiene may be efficiently separated.

A stream B4 generated after the condensation separation process may contain crude hydrocarbons including n-butane, butene, and butadiene, which are condensed in the condensation separation part 230. The discharge stream B4 may be introduced into a purification part 240, and butadiene may be purified.

A discharge stream B5 generated after the absorption separation process may contain $O_2$, COx, and the like, which are separated in the previous condensation separation process, and a discharge stream B6 generated after the absorption separation process may contain hydrocarbons including n-butane, butene, butadiene, and the like, which are selectively absorbed to a solvent in the absorption separation part 250. Recirculation streams, in which the streams B6 are fed again into the condensation separation part 230, are formed, and condensation separation of $O_2$, COx, and the like may be performed.

A discharge stream B7 generated after the purification process may contain a large amount of residual n-butane, and a recirculation stream, in which the stream is fed again into the oxidative dehydrogenation reaction part 210, may be formed. A discharge stream B8 containing butene remaining after butadiene is separated in the purification part 240 may be mixed with butene supplied as a raw material and fed again into the oxidative dehydrogenation reaction part, thereby forming a recirculation stream.

The term "crude hydrocarbons" refers to crude hydrocarbons commonly used in the art to which the present invention pertains. Unless otherwise specified herein, the crude hydrocarbons refer to hydrocarbons including butadiene and the like recovered from oxidative dehydrogenation reaction products, and are used as raw materials in the purification part.

The term "COx" refers to, unless otherwise specified herein, CO and $CO_2$.

In the present invention, butene may be 1-butene, 2-butene, or a mixture thereof. Raw material gases containing butene generally used to prepare butadiene are not particularly limited and may be used as the raw material gases containing butene of the present invention.

For example, butene may be obtained from a hydrocarbon mixture including butenes, such as raffinate-2 and raffinate-3, included in the C4 fraction produced when a high-purity butene gas and naphtha are decomposed.

The steam is a gas which is injected for the purpose of preventing coking of a catalyst and removing heat of reaction while reducing risk of explosion of reactants when oxidative dehydrogenation is performed.

In the present invention, oxygen ($O_2$) reacts with butene as an oxidizing agent to cause dehydrogenation.

Any catalysts may be used as the catalyst of the present invention packed in the reactor without any particular limitation as long as the catalysts are capable of catalyzing oxidative dehydrogenation of butene to prepare butadiene. For example, ferrite catalysts or bismuth molybdate catalysts may be included.

In one embodiment of the present invention, the catalyst may be a ferrite catalyst. In particular, when zinc ferrite, magnesium ferrite, or manganese ferrite is used, selectivity for butadiene may be increased. The kind and amount of the reaction catalyst may vary depending on specific reaction conditions.

The diluent gas may be butane. In this case, the diluent gas refers to a gas which circulates through reaction, and is different from a noncombustible diluent gas injected to prevent explosion reaction in the absorption separation part 250.

For example, the oxidative dehydrogenation reaction part 210 may be operated under isothermal or adiabatic conditions, in which case butene, oxygen ($O_2$), steam, and a gas containing n-butane are used as reaction raw materials, and a ferrite catalyst or a bismuth molybdate catalyst is used as a catalyst, wherein n-butane is a residue remaining after butadiene is separated in the purification part 240 and are fed again into the oxidative dehydrogenation reaction part.

For example, oxygen ($O_2$) contained in the reaction raw materials may be fed in a gaseous form having a purity of 90% or more, 95% or more, or 8% or more.

Feeding of oxygen ($O_2$) in a gaseous form having a purity of 90% or more means that oxygen is not supplied from air, but is fed in a pure oxygen form. Thus, by measuring the amount of active ingredients contained in reaction raw materials in real time, it is possible to control the amount of each of the components contained in reaction raw materials fed into a reactor.

For example, in the oxidative dehydrogenation reaction part 210, oxidative dehydrogenation may be performed in a molar ratio of butene:oxygen:steam:diluent gas (n-butane)=1:0.5 to 5:0.1 to 20:0.1 to 20.

As a particular example, the oxidative dehydrogenation reaction part 210 is preferably operated in a molar ratio of oxygen:butene=0.5 to 5:1, a molar ratio of steam:butene=0.1 to 20:1, and a molar ratio of n-butane:butene=0.1 to 20:1 at a reaction pressure of atmospheric pressure to 10 atm and a reaction temperature of 150 to 650° C. under isothermal or adiabatic conditions.

For example, the cooling separation part 220 may be operated by a quenching-type direct cooling system (quencher) or an indirect cooling system. In this case, the cooling separation part may be rapidly cooled to a temperature of 0 to 50° C.

For example, the condensation separation part 230 may have a single-stage compression structure having one stage or a multistage compression structure having 2 to 10 stages or 1 to 2 stages. When compressing from an initial pressure to a target pressure, a lot of power is required. In addition, heat is generated due to gas compression, which causes gas expansion, resulting in poor compression efficiency. Therefore, to prevent such problems, multi-stage compression is performed. In this case, heat generated in the compression process may be dissipated using a cooler.

In the condensation separation part 230, condensation conditions may be determined so that the stream of the condensation separation part 230 is out of an explosive range in consideration of unreacted oxygen (i.e., above upper explosive limit or below limiting oxygen concentration).

In one embodiment of the present invention, a refrigerant used in the condensation separation part 230 may be one or more selected from the group consisting of cooling water, ethylene glycol, an aqueous solution of ethylene glycol having a concentration of 20 to 100% by weight, propylene glycol, an aqueous solution of propylene glycol having a concentration of 30 to 100% by weight, and a propylene-based solvent, preferably cooling water. For example, the propylene-based solvent, as a compound including propylene or propylene, may have a boiling point of −10° C. or less or −10 to −50° C.

For example, the refrigerant is preferably cooling water, cooling water having a temperature of 0 to 40° C., or cooling water having a temperature of 5 to 30° C. In this case, the extrusion discharge temperature may be 250° C. or less or 50 to 250° C., and the cooling temperature of a compression discharge stream may be 120° C. or less or 20 to 80° C.

Conventionally, since nitrogen is used as a diluent gas, a very low-temperature refrigerant is required when a dilution gas and light gas species are separated using a condensation method. In the present invention, since butane is used as a diluent gas, a lower grade of refrigerant may be used.

For example, a conventional apparatus for purifying butadiene may be used as the purification part 240. When necessary, in the purification part 240, a process capable of using separated butadiene, such as an acetonitrile (ACN) process, a N-methylpyrrolidone (NMP) process, or a dimethyl formamide (DMF) process may be performed.

For example, the absorption separation part 250 may be operated in an absorption manner using acetonitrile (ACN), N-methylpyrrolidone (NMP), or dimethyl formamide (DMF) capable of selectively absorbing hydrocarbons when hydrocarbons are separated from COx, $O_2$, and a noncombustible diluent gas under the conditions that a noncombustible diluent gas is fed. The amount of the noncombustible diluent gas injected into the absorption separation part 250 should be controlled so that the ratio of combustible gas oxidizing gas noncombustible gas deviates from an explosive range. For example, the input amount of the noncombustible diluent gas may be adjusted so that oxygen concentration is below limiting oxygen concentration, or so that the ratio of noncombustible gas:oxygen:fuel is higher than upper explosive limit or lower than lower explosion limit.

For example, the noncombustible diluent gas may be nitrogen, argon, helium, or carbon dioxide.

Heat generated when COx, $O_2$, and noncombustible diluent gas separated in the absorption separation part 250 are incinerated may be reused in the oxidative dehydrogenation reaction part 210 or the condensation separation part 230.

In a purification step, solvents, high boiling point components, and low boiling point components are removed from crude hydrocarbons including n-butane, butene, and butadiene, which are obtained in the condensation separation step and absorption separation step, and thus high-purity butadiene may be obtained.

In one embodiment of the present invention, the purity of finally obtained butadiene through the series of steps described above may be 95.0 to 99.9%.

Figure 3:
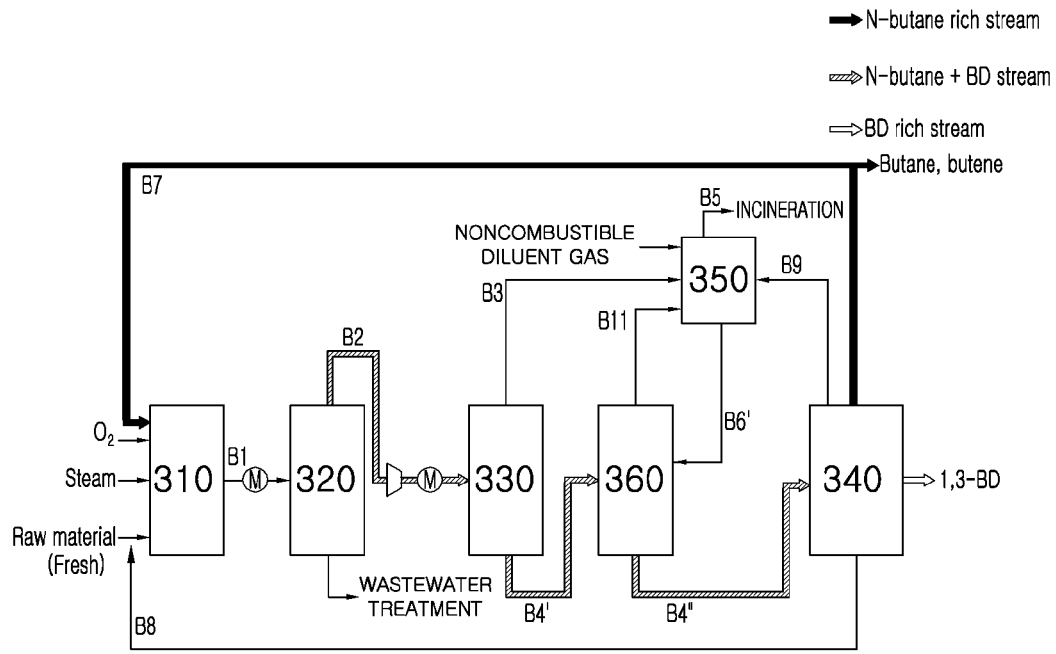

FIG. 3 is a schematic diagram showing a process of separating COx and $O_2$ by passing hydrocarbons not condensed in a condensation separation part 330 in FIG. 2 through an absorption separation part 350 under the conditions that a noncombustible diluent gas is fed, and a process, in which a discharge stream containing COx and $O_2$, which are additionally separated by passing butene, oxygen ($O_2$), steam, and a diluent gas (butane) condensed in the condensation separation part through a degasification part, is passed through an absorption separation part, and crude hydrocarbons including n-butane, butene, and butadiene, from which COx and $O_2$ are additionally removed in a degasification part, are passed through a purification part to separate butadiene. At this time, the process is explained including the degasification part. Through the process, hydrocarbons may be condensed and selectively absorbed/recovered.

For example, the degasification part may be operated by stripping using a conventional column, or degasification.

Referring to FIG. 3, first, oxidative dehydrogenation reaction products containing butadiene are obtained by passing reaction raw materials containing butene, oxygen ($O_2$), steam, and a diluent gas (butane) through an oxidative dehydrogenation reaction part 310. At this time, raw materials for oxidative dehydrogenation may be combined with the discharge streams B7 and B8 resulting from a purification process, and introduced into the oxidative dehydrogenation reaction part 310. The stream B1 discharged from the process may include butadiene, n-butane, butene, $O_2$, COx, $H_2O$, and the like.

The stream B1 discharged from the oxidative dehydrogenation reaction part 310 is introduced into a cooling separation part 320, and water is separated from the stream B1.

The discharge stream B2 generated after the cooling separation process may contain butadiene, n-butane, butene, $O_2$, COx, and the like. The discharge stream B2 is introduced into the condensation separation part 330.

The discharge stream B3 generated after the condensation separation process may contain oxidative dehydrogenation reaction products containing hydrocarbons, which are not condensed after condensation of hydrocarbons is performed using cooling water, and the like according to a compression/cooling manner in the condensation separation part.

The discharge stream B3 may be introduced into the absorption separation part 350, and hydrocarbons may be recovered therefrom under the conditions that a noncombustible diluent gas is fed. Another discharge stream B4' generated after the condensation separation process may contain hydrocarbons including n-butane, butene, and butadiene, which are condensed in the condensation separation part 330. The discharge stream B4' may be introduced into a degasification part 360, and COx and $O_2$ may be additionally separated therefrom.

A discharge stream B4" containing crude hydrocarbons including n-butane, butene, and butadiene, which are condensed after COx and $O_2$ are additionally separated in the degasification part 360, may be introduced into a purification part 340, and butadiene may be purified from the discharge stream B4". Another discharge stream B11 generated after the degasification process may contain COx and $O_2$ additionally separated in the degasification part 360. The discharge stream B11 may be introduced into the absorption separation part 350, and COx, $O_2$, and a noncombustible diluent gas may be absorbed and separated from the discharge stream B11 under the conditions that the noncombustible diluent gas is injected.

The discharge stream B5 generated after the absorption separation process may contain $O_2$, COx, and the like separated in the previous condensation separation process and the noncombustible diluent gas introduced into the absorption separation process. Another discharge stream B6' generated after the absorption separation process may contain hydrocarbons including n-butane, butene, butadiene, and the like, which are selectively absorbed in the absorption separation part 350, and a certain amount of COx and $O_2$. The discharge stream B6' may be introduced into the degasification part 360, resulting in formation of a recirculation stream.

A discharge stream B9 generated after a solvent is separated in the purification part 340 may be circulated to the absorption separation part 350, and the discharge stream B8 containing residual butene remaining after butadiene and a solvent are separated may be mixed with butene supplied as a raw material, and introduced into the oxidative dehydrogenation reaction part 310. This process flow is preferred because the reaction may proceed continuously. The discharge stream B7 generated after the purification process may contain a large amount of residual n-butane, and may be introduced into the oxidative dehydrogenation reaction part 310, resulting in formation of a recirculation stream.

Figure 4:
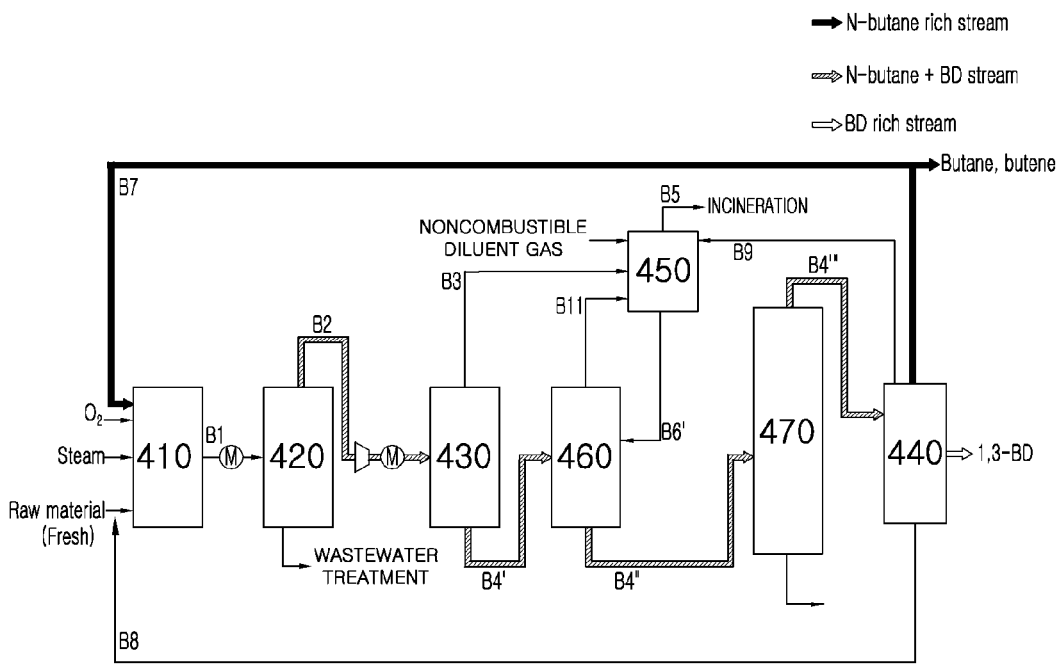

FIG. 4 is a schematic diagram showing a process, in which another discharge stream B4''' is additionally added to the discharge stream B4" generated after the degasification process in FIG. 3. The discharge stream B4" may contain crude hydrocarbons including n-butane, butene, and butadiene excluding COx and $O_2$, which are additionally separated in a degasification part 460, and may be fed into a high-boiling point material removal part 470 to remove high-boiling point materials. The discharge stream B4''' generated after the high-boiling point materials are removed may contain crude hydrocarbons, of which boiling point is lowered by removing high-boiling point components. The crude hydrocarbons may be passed through a purification part 440 to efficiently purify butadiene.

For example, the high-boiling point material removal part may be operated in a distillation manner.

For example, the high-boiling point materials may be aromatic hydrocarbons, such as furans, aldehydes, acetic acid, benzene, and phenol, or styrene.

Referring to FIG. 4, first, reaction raw materials containing butene, oxygen ($O_2$), steam, and a diluent gas (butane) are passed through an oxidative dehydrogenation reaction part 410 to obtain oxidative dehydrogenation reaction products containing butadiene. At this time, raw materials for oxidative dehydrogenation may be combined with the discharge streams B7 and B8 resulting from a purification process and introduced into the oxidative dehydrogenation reaction part 410. The stream B1 discharged after the process may contain butadiene, n-butane, butene, $O_2$, COx, $H_2O$, and the like. The stream B1 discharged from the oxidative dehydrogenation reaction part 410 is introduced into a cooling separation part 420, and water is separated therefrom.

The discharge stream B2 generated after the cooling separation process may contain butadiene, n-butane, butene, $O_2$, COx, and the like, and may be introduced into a condensation separation part 430.

The discharge stream B3 generated after the condensation separation process may contain oxidative dehydrogenation reaction products including hydrocarbons not condensed when hydrocarbons are condensed using cooling water through compression/cooling in the condensation separation process.

The discharge stream B3 may be introduced into an absorption separation part 450, and hydrocarbons may be recovered from the discharge stream B3 under the conditions that a noncombustible diluent gas is fed.

Another discharge stream B4' generated after the condensation separation process may contain hydrocarbons including n-butane, butene, and butadiene, which are condensed in the condensation separation part 430. The discharge stream B4' may be introduced into the degasification part 460, and COx and $O_2$ may be additionally separated therefrom.

The discharge stream B11 generated after the degasification process may contain COx and $O_2$ additionally separated in the degasification part 460. The discharge stream B11 may be introduced into the absorption separation part 450, and COx, $O_2$, and a noncombustible diluent gas may be absorbed and separated from the discharge stream B11 under the conditions that the noncombustible diluent gas is fed.

Another discharge stream B4" generated after the degasification process may contain crude hydrocarbons including n-butane, butene, and butadiene excluding COx and $O_2$ additionally separated in the degasification part 460. The discharge stream B4''' generated after high-boiling point materials are separated in the high-boiling point material removal part 470 may contain crude hydrocarbons, of which boiling point is lowered by removing high-boiling point components. The crude hydrocarbons may be introduced into the purification part 440 to purify butadiene.

The discharge stream B5 generated after the absorption separation process may contain $O_2$, COx, and the like separated in the previous condensation separation process and a noncombustible diluent gas introduced during the absorption separation process. Another discharge stream B6' generated after the absorption separation process may contain hydrocarbons including n-butane, butene, butadiene, and the like, which are absorbed in a solvent in the absorption separation part 450, and a certain amount of COx and O2. The discharge stream B6' may be fed into the degasification part 460, resulting in formation of a recirculation stream.

The discharge stream B7 generated after the purification process may contain a large amount of residual n-butane, and may be fed into the oxidative dehydrogenation reaction part 410, resulting in formation of a recirculation stream. A discharge stream containing residual butene remaining after butadiene is separated in the purification part 440 may be mixed with butene supplied as a raw material, and introduced into the oxidative dehydrogenation reaction part, resulting in formation of a recirculation stream. In this case, reaction proceeds in a continuous manner, so that raw material costs may be reduced and productivity may be improved.

As shown in FIG. 3, the discharge stream B9 containing a solvent separated in the purification part 440 may be circulated to the absorption separation part 450, and the discharge stream B8 containing residual butene remaining after butadiene and a solvent are separated may be mixed with butene supplied as a raw material, and introduced into the oxidative dehydrogenation reaction part 410. In this case, reaction proceeds in a continuous manner, so that productivity and economic efficiency may be improved.

Figure 5:
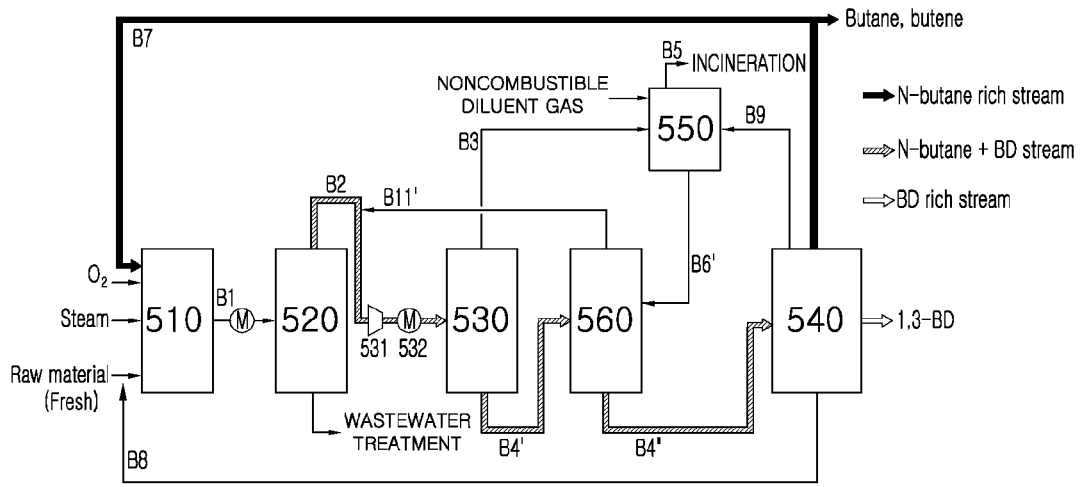

FIG. 5 is a schematic diagram showing a case where the discharge stream B11 generated after the degasification process in FIG. 3 is replaced with another discharge stream B11'. In this case, gas separation efficiency may be improved by feeding COx and $O_2$ separated in a degasification part 560 into the condensation system.

Referring to FIG. 5, first, reaction raw materials containing butene, oxygen ($O_2$), steam, and a diluent gas (butane) are passed through an oxidative dehydrogenation reaction part 510 to obtain oxidative dehydrogenation reaction products containing butadiene. At this time, raw materials for oxidative dehydrogenation may be combined with the discharge streams B7 and B8 resulting from a purification process, and introduced into the oxidative dehydrogenation reaction part 510. The stream B1 discharged after the process may contain butadiene, n-butane, butene, $O_2$, COx, $H_2O$, and the like. The stream B1 discharged from the oxidative dehydrogenation reaction part 510 is introduced into a cooling separation part 520, and water is separated therefrom.

The discharge stream B2 generated after the cooling separation process may contain butadiene, n-butane, butene, $O_2$, COx, and the like, and may be introduced into a condensation separation part 530.

The discharge stream B3 generated after the condensation separation process may contain hydrocarbons not condensed when hydrocarbons are condensed using cooling water through compression/cooling in the condensation separation process. The discharge stream B3 may be introduced into an absorption separation part 550, and hydrocarbons may be recovered under the conditions that a noncombustible diluent gas is injected. Another discharge stream B4' generated after the condensation separation process may contain hydrocarbons n-butane, butene and, butadiene, which are condensed in the condensation separation part 530. The discharge stream B4' may be introduced into the degasification part 560, and COx and $O_2$ may be additionally separated therefrom.

The discharge stream B4" containing crude hydrocarbons including n-butane, butene, and butadiene, which are condensed after COx and $O_2$ are additionally separated in the degasification part 560, may be introduced into a purification part 540, and butadiene may be purified. Another discharge stream B11' generated after the degasification process may contain COx and $O_2$, which are additionally separated in the degasification part 560. The discharge stream B11' may be fed into the condensation system, and recondensation and separation may be performed in the condensation separation part 530.

Unless otherwise specified herein, the condensation system refers to a system including a compressor 531, a heat exchanger 532, and the condensation separation part 530.

The discharge stream B5 generated after the absorption separation process may contain $O_2$ and COx not separated in the previous cooling separation process and a noncombustible diluent gas fed in the absorption separation part 550. Another discharge stream B6' generated after the absorption separation process may contain hydrocarbons including n-butane, butene, and butadiene, which are absorbed in a solvent in the absorption separation part 550, and a certain amount of COx and $O_2$. The discharge stream B6' is fed again into the degasification part 560.

The discharge stream B9 containing a solvent separated in the purification part 540 may be circulated to the absorption separation part 550. The discharge stream B8 containing residual butene remaining after butadiene and a solvent are separated may be mixed with butene supplied as a raw material, and introduced into the oxidative dehydrogenation reaction part 510. In this case, reaction proceeds in a continuous manner, so that productivity and economic efficiency may be improved.

Figure 6:
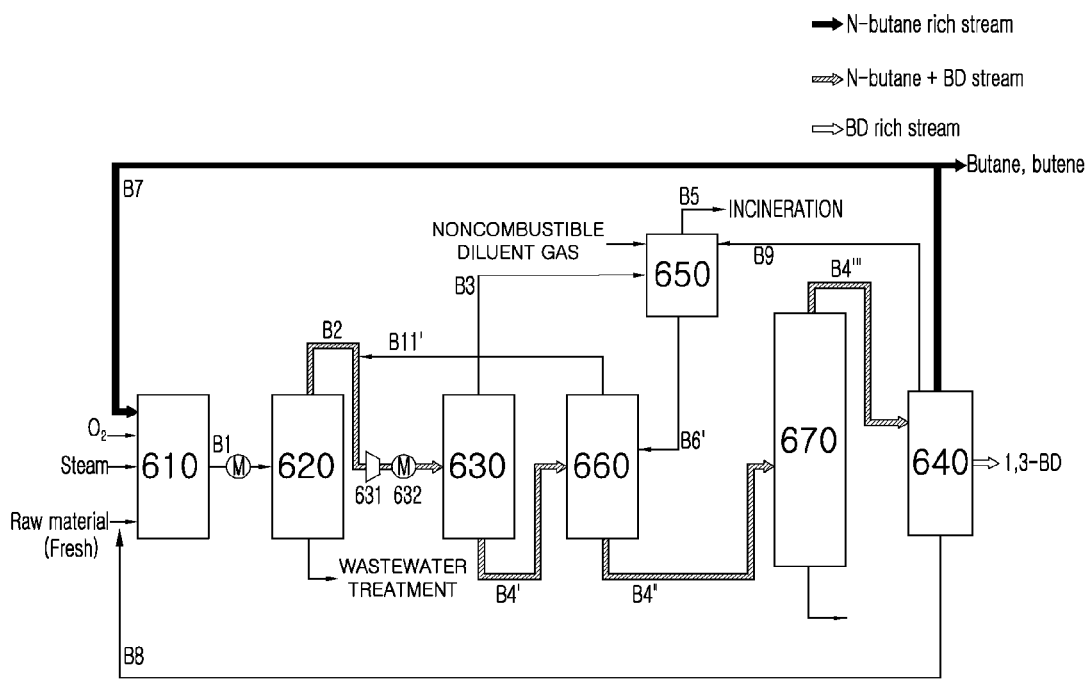

FIG. 6 is a schematic diagram showing a case where the discharge stream B11 generated after the degasification in FIG. 4 is replaced with another discharge stream B11'. In this case, COx and $O_2$ separated in a degasification part 660 are fed into the condensation system, and thus COx and $O_2$ are fed again into a condensation separation part 630, thereby improving gas separation efficiency.

Referring to FIG. 6, first, reaction raw materials containing butene, oxygen ($O_2$), steam, and a diluent gas (butane) are passed through an oxidative dehydrogenation reaction part 610 to obtain oxidative dehydrogenation reaction products containing butadiene. At this time, raw materials for oxidative dehydrogenation may be combined with the discharge streams B7 and B8 resulting from a purification process, and introduced into the oxidative dehydrogenation reaction part 610. The stream B1 discharged after the process may contain butadiene, n-butane, butene, $O_2$, COx, $H_2O$, and the like. The stream B1 discharged from the oxidative dehydrogenation reaction part 610 is introduced into a cooling separation part 620, and water is separated therefrom.

The discharge stream B2 generated after the cooling separation process may contain butadiene, n-butane, butene, $O_2$, COx, and the like, and may be introduced into the condensation separation part 630.

The discharge stream B3 generated after the condensation separation process may contain oxidative dehydrogenation reaction products including hydrocarbons not condensed when hydrocarbons are condensed using cooling water through compression/cooling in the condensation separation process.

The discharge stream B3 generated after the condensation separation process may be introduced into an absorption separation part 650, and hydrocarbons may be recovered from the discharge stream B3 under the conditions that a noncombustible diluent gas is injected. Another discharge stream B4' generated after the condensation separation process may contain hydrocarbons including n-butane, butene, and butadiene, which are condensed in the condensation separation part 630. The discharge stream B4' may be introduced into the degasification part 660, and COx and $O_2$ may be additionally separated therefrom.

The discharge stream B11' generated after the degasification process may contain COx and $O_2$ additionally separated in the degasification part 660, and may be introduced into the condensation system, and recondensation separation may be performed in the condensation separation part 630.

Unless otherwise specified herein, the condensation system refers to a system including a compressor 631, a heat exchanger 632, and the condensation separation part 630.

Another discharge stream B4" generated after the degasification process may contain crude hydrocarbons including n-butane and butadiene excluding COx and $O_2$, which are additionally separated in the degasification part 660. The discharge stream B4" is passed through a high-boiling point material removal part 670 to separate high-boiling point components.

For example, the high-boiling point materials may be aromatic hydrocarbons, such as furans, aldehydes, acetic acid, benzene, and phenol, or aromatic hydrocarbons, or styrene.

The discharge stream B4''' generated after high-boiling point materials are separated may contain crude hydrocarbons, of which boiling point is lowered by removing high-boiling point components. Butadiene may be purified by passing the crude hydrocarbons into a purification part 640.

The discharge stream B5 generated after the absorption separation process may contain $O_2$, COx, and the like, which are separated in the previous condensation separation process, and a noncombustible diluent gas fed into the absorption separation part. The discharge stream B6' generated after the absorption separation process may contain hydrocarbons including n-butane, butene, butadiene, and the like, which are absorbed in a solvent in the absorption separation part 650, and a certain amount of COx and $O_2$. The discharge stream B6' may be fed again into the degasification part 660, resulting in formation of a recirculation stream.

The discharge stream B7 generated after the purification process may contain a large amount of residual n-butane, and may be fed into the oxidative dehydrogenation reaction part 610, resulting in formation of a recirculation stream. The discharge stream B8 containing residual butene remaining after butadiene is separated in the purification part 640 may be fed into the oxidative dehydrogenation reaction part 610, resulting in formation of a recirculation stream. In this case, reaction proceeds in a continuous manner, so that raw material costs may be reduced and productivity may be improved.

As shown in FIG. 4, the discharge stream B9 containing a solvent separated in the purification part 640 may be circulated to the absorption separation part 650.

For example, a device used in the method of the present invention, referring to FIG. 2, includes the oxidative dehydrogenation reaction part 210, in which oxidative dehydrogenation of reaction raw materials containing butene, oxygen ($O_2$), steam, and a diluent gas (butane) is performed to obtain oxidative dehydrogenation reaction products containing butadiene; a cooling separation part 220 responsible for separating water from the oxidative dehydrogenation reaction products containing butadiene; the condensation separation part 230 responsible for condensing hydrocarbons from the oxidative dehydrogenation reaction products, from which water is separated; the absorption separation part 250 responsible for separating COx, $O_2$, and a noncombustible diluent gas from oxidative dehydrogenation reaction products containing hydrocarbons not condensed in the condensation separation part 230 under the conditions that a noncombustible diluent gas is fed; and the purification part 240 responsible for separating butadiene from crude hydrocarbons including n-butane, butene, and butadiene, which are condensed in the condensation separation part 230, wherein these parts are configured to have the discharge stream B7, through which gas containing n-butane excluding butadiene separated in the purification part 240 is fed again into the oxidative dehydrogenation reaction part 210.

The device is configured to have the discharge stream B8, through which a discharge stream containing butene remaining after butadiene is separated in the purification part 240 is mixed with butene supplied as a raw material, and fed again into the oxidative dehydrogenation reaction part 210.

The device is configured so that the discharge stream B6 containing hydrocarbons including n-butane, butene, and butadiene excluding COx, $O_2$, and a noncombustible diluent gas, which are separated in the absorption separation part 250 under the conditions that a noncombustible diluent gas is fed, is fed again into the condensation separation part 230.

For example, the noncombustible dilute gas may be nitrogen gas ($N_2$), argon, helium, or carbon dioxide ($CO_2$).

As another example, a device for preparing butadiene, referring to FIG. 3, includes the oxidative dehydrogenation reaction part 310, in which oxidative dehydrogenation of reaction raw materials containing butene, oxygen ($O_2$), steam, and a diluent gas (butane) is performed to obtain oxidative dehydrogenation reaction products containing butadiene; a cooling separation part 320 responsible for separating water from the oxidative dehydrogenation reaction products containing butadiene; the condensation separation part 330 responsible for condensing hydrocarbons from the oxidative dehydrogenation reaction products, from which water is separated; the absorption separation part 350 responsible for separating COx, $O_2$, and a noncombustible diluent gas and hydrocarbons including n-butane, butene, and butadiene from oxidative dehydrogenation reaction products containing hydrocarbons not condensed in the condensation separation part 330 under the conditions that a noncombustible diluent gas is fed; the degasification part 360 responsible for separating COx and $O_2$ and hydrocarbons including n-butane, butene, and butadiene from oxidative dehydrogenation reaction products containing hydrocarbons condensed in the condensation separation part 330; and the purification part 340 responsible for separating butadiene from crude hydrocarbons including n-butane, butene, and butadiene excluding Cox and $O_2$, which are separated in the degasification part 360, wherein these parts are configured to have the discharge streams B9 and B7, wherein the discharge stream B9 is responsible for circulating a solvent separated in the purification part 340 to the absorption separation part 350, and the discharge stream B7 is responsible for refeeding gas containing n-butane excluding butadiene and the solvent into the oxidative dehydrogenation reaction part 310.

The device is configured to have the discharge stream B8, through which a discharge stream containing butene remaining after butadiene is separated in the purification part 340 is mixed with butene supplied as a raw material, and fed again into the oxidative dehydrogenation reaction part 310.

The device is configured so that the discharge stream B6' containing hydrocarbons including n-butane, butene, and butadiene excluding COx, $O_2$, and a noncombustible diluent gas, which are separated in the absorption separation part 350 under the conditions that a noncombustible diluent gas is fed, is introduced into the degasification part 360, resulting in formation of a recirculation stream.

The device is configured so that the discharge stream B11 containing COx, $O_2$, and a noncombustible diluent gas, which are separated in the degasification part 360 under the conditions that a noncombustible diluent gas is fed, is circulated to the absorption separation part 350, and the discharge stream B6' containing hydrocarbons including n-butane, butene, and butadiene, which are absorbed in a solvent in the absorption separation part 350, is recirculated to the degasification part 360 recirculation.

As another example, a device for preparing butadiene, referring to FIG. 4, includes the oxidative dehydrogenation reaction part 410, in which oxidative dehydrogenation of reaction raw materials containing butene, oxygen ($O_2$), steam, and a diluent gas (butane) is performed to obtain oxidative dehydrogenation reaction products containing butadiene; a cooling separation part 420 responsible for separating water from the oxidative dehydrogenation reaction products containing butadiene; the condensation separation part 430 responsible for condensing hydrocarbons from the oxidative dehydrogenation reaction products, from which water is separated; the absorption separation part 450 responsible for separating COx, $O_2$, and a noncombustible diluent gas from oxidative dehydrogenation reaction products containing hydrocarbons not condensed in the condensation separation part 430 under the conditions that a noncombustible diluent gas is fed; the degasification part 460 responsible for separating COx and $O_2$ from hydrocarbons including n-butane, butene, and butadiene, which are condensed in the condensation separation part 430; the high-boiling point material removal part 470 responsible for removing high-boiling point materials from crude hydrocarbons including n-butane, butene, and butadiene, from which COx and $O_2$ are removed in the degasification part 460; and the purification part 440 responsible for separating butadiene from crude hydrocarbons, from which the high-boiling point materials are removed, wherein these parts are configured to have the discharge streams B9 and B7, wherein the discharge stream B9 is responsible for circulating a solvent separated in the purification part 440 to the absorption separation part 450, and the discharge stream B7 is responsible for refeeding gas containing n-butane excluding butadiene and the solvent into the oxidative dehydrogenation reaction part 410.

The device is configured to have the discharge stream B8, through which a discharge stream containing residual butene remaining after butadiene is separated in the purification part 440 is mixed with butene supplied as a raw material, and fed again into the oxidative dehydrogenation reaction part 410.

The device is configured so that the discharge stream B6' containing n-butane, butene, and butadiene excluding COx, $O_2$, and a noncombustible diluent gas, which are separated in the absorption separation part 450 under the conditions that a noncombustible diluent gas is fed, is recirculated to the degasification part 460.

The device is configured so that the discharge stream B11 containing COx, $O_2$, and a noncombustible diluent gas, which are separated in the degasification part 460 under the conditions that a noncombustible diluent gas is fed, is circulated to the absorption separation part 450, and the discharge stream B6' containing hydrocarbons including n-butane, butene, and butadiene, which are absorbed in a solvent in the absorption separation part 450, is recirculated to the degasification part 460.

The device is configured so that the discharge stream B4''' containing crude hydrocarbons including n-butane, butene, and butadiene, which are separated in the degasification part 460, is fed into the high-boiling point material removal part 470 to remove high-boiling point materials, and the discharge stream B4''' containing crude hydrocarbons, from which the high-boiling point materials are removed, is fed into the purification part 440.

As another example, a device for preparing butadiene, referring to FIG. 5, includes the oxidative dehydrogenation reaction part 510, in which oxidative dehydrogenation of reaction raw materials containing butene, oxygen ($O_2$), steam, and a diluent gas (butane) is performed to obtain oxidative dehydrogenation reaction products containing butadiene; a cooling separation part 520 responsible for separating water from the oxidative dehydrogenation reaction products containing butadiene; the condensation separation part 530 responsible for condensing hydrocarbons from the oxidative dehydrogenation reaction products, from which water is separated; the absorption separation part 550 responsible for separating COx, $O_2$, and a noncombustible diluent gas from oxidative dehydrogenation reaction products including hydrocarbons not condensed in the condensation separation part 530 under the conditions that a noncombustible diluent gas is fed; the degasification part 560 responsible for separating COx and $O_2$ from hydrocarbons including n-butane, butene, and butadiene, which are condensed in the condensation separation part 530; and the purification part 540 responsible for separating butadiene from crude hydrocarbons including n-butane, butene, and butadiene excluding COx and $O_2$, which are separated in the degasification part 560, wherein these parts are configured to have the discharge streams B9 and B7, wherein the discharge streams B9 is responsible for circulating a solvent separated in the purification part 540 to the absorption separation part 550, and the discharge stream B7 is responsible for refeeding gas containing n-butane excluding butadiene and the solvent into the oxidative dehydrogenation reaction part 510.

The device is configured to have the discharge stream B8, through which a discharge stream containing residual butene remaining after butadiene is separated in the purification part 540 is mixed with butene supplied as a raw material, and fed again into the oxidative dehydrogenation reaction part 510.

The device is configured so that the discharge stream B6' containing hydrocarbons including n-butane, butene, and butadiene, which are obtained after COx, $O_2$, and a noncombustible diluent gas are separated from the absorption separation part 550 under the conditions that a noncombustible diluent gas is fed, is recirculated into the degasification part 560.

The device is configured so that the discharge stream B11' containing COx and $O_2$ separated in the degasification part 560 is fed into the condensation system, and recondensed in the condensation separation part 530.

Unless otherwise specified herein, the condensation system refers to a system including the compressor 531, the heat exchanger 532, and the condensation separation part 530.

As another example, a device for preparing butadiene, referring to FIG. 6, includes the oxidative dehydrogenation reaction part 610, in which oxidative dehydrogenation of reaction raw materials containing butene, oxygen ($O_2$), steam, and a diluent gas (butane) is performed to obtain oxidative dehydrogenation reaction products containing butadiene; a cooling separation part 620 responsible for separating water from the oxidative dehydrogenation reaction products containing butadiene; the condensation separation part 630 responsible for condensing hydrocarbons from the oxidative dehydrogenation reaction products, from which water is separated; the absorption separation part 650 responsible for separating COx, $O_2$, and a noncombustible diluent gas from oxidative dehydrogenation reaction products including hydrocarbons not condensed in the condensation separation part 630 under the conditions that a noncombustible diluent gas is fed; the degasification part 660 responsible for separating COx and $O_2$ from hydrocarbons including n-butane, butene, and butadiene, which are condensed in the condensation separation part 630; the high-boiling point material removal part 670 responsible for removing high-boiling point materials from crude hydrocarbons including n-butane, butene, and butadiene excluding COx and $O_2$, which are separated in the degasification part 660; and the purification part 640 responsible for separating butadiene from crude hydrocarbons, from which the high-boiling point materials are removed, wherein these parts are configured to have the discharge streams B9 and B7, wherein the discharge stream B9 is responsible for circulating a solvent separated in the purification part 640 to the absorption separation part 650, and the discharge stream B7 is responsible for refeeding gas containing n-butane excluding butadiene and the solvent into the oxidative dehydrogenation reaction part 610.

The device is configured to have the discharge stream B8, through which a discharge stream containing residual butene remaining after butadiene is separated in the purification part 640 is mixed with butene supplied as a raw material, and fed again into the oxidative dehydrogenation reaction part 610.

The device is configured so that the discharge stream B6' containing hydrocarbons including n-butane, butene, and butadiene excluding COx, $O_2$, and a noncombustible diluent gas, which are separated in the absorption separation part 650 under the conditions that a noncombustible diluent gas is fed, is fed into the degasification part 660.

The device is configured so that the discharge stream B11' containing COx, $O_2$, and a noncombustible diluent gas, which are separated in the degasification part 660 under the conditions that a noncombustible diluent gas is fed, is fed into the condensation system, and recondensed in the condensation separation part 630.

Unless otherwise specified herein, the condensation system refers to a system including the compressor 631, the heat exchanger 632, and the condensation separation part 630.

The device is configured so that the discharge stream B4" containing crude hydrocarbons including n-butane, butene, and butadiene, which are separated in the degasification part 660, is fed into the high-boiling point material removal part 670 to separate high-boiling point materials, and the discharge stream B4'" containing crude hydrocarbons, from which the high-boiling point materials are removed, is fed into the purification part 640.

A heat exchange means may be provided between the absorption separation parts 250, 350, 450, 550, and 650 and the oxidative dehydrogenation reaction parts 210, 310, 410, 510, and 610, between the absorption separation parts 250, 350, 450, 550, and 650 and the condensation separation parts 240, 340, 440, 540, and 640, or between the absorption separation parts 250, 350, 450, 550, and 650, the oxidative dehydrogenation reaction parts 210, 310, 410, 510, and 610, and the condensation separation parts 240, 340, 440, 540, and 640, so that heat generated when COx, $O_2$, and a noncombustible diluent gas, which are separated in the absorption separation parts 250, 350, 450, 550, and 650 under the conditions that a noncombustible diluent gas is fed, are incinerated, is reused to heat raw materials, or reused in purification parts 240, 340, 440, 540, and 640.

In summary, when the method of preparing butadiene and the device for preparing the same according to the present invention are used, the disadvantages of conventional butadiene preparation methods, in which nitrogen is used as a diluent gas, may be overcome, and process efficiency may be improved. That is, use of the method and device of the present invention may minimize the amount of active ingredients discharged to the outside of the system during processes, thereby improving productivity and stability. In addition, since the method of preparing butadiene according to the present invention may be directly used for purification/separation of various materials (ACN, NMP, DMF, and the like) described above, the method of the present invention may be applied to various processes.

Hereinafter, the present invention will be described in more detail with reference to the following preferred examples. However, these examples are provided for illustrative purposes only and should not be construed as limiting the scope and spirit of the present invention. In addition, it will be apparent to those skilled in the art that various changes and modifications may be made without departing from the spirit and scope of the present invention, and such changes and modifications are also within the scope of the appended claims.

EXAMPLE

Example 1

To obtain oxidative dehydrogenation reaction products containing butadiene, oxidative dehydrogenation of reaction raw materials including butene, steam, and butane in molar ratios of butene:oxygen=1:0.9, butene:steam=1:5, and butene:butane=1:4 was performed in the presence of a ferrite catalyst in the device for preparing butadiene according to FIG. 2. In this case, butane was used as a diluent gas, and raffinate-3 having compositions shown in Table 1 below was used as a butene source. Then, in the cooling separation part, water was removed from the obtained oxidative dehydrogenation reaction products. The water-removed oxidative dehydrogenation reaction products were introduced into the condensation separation part, and pressurized at a pressure of 8 KCG and a cooling temperature of 35° C. using a two-stage compressor, and hydrocarbons were condensed at 40° C. using cooling water. Thereafter, nitrogen was injected into the absorption separation part so that the molar concentration of oxygen became 9 mol %, so that a vapor phase stream was out of an explosive range. Then, DMF was used as a solvent, and hydrocarbons were selectively absorbed to obtain crude hydrocarbons. In the purification part, butadiene was purified and recovered from the crude hydrocarbons using DMF as a solvent.

In this case, the discharge stream of the oxidative dehydrogenation reaction part was analyzed using gas chromatography. The compositions of the discharge streams B1 to B8 of each of the cooling separation part, the condensation separation part, the absorption separation part, and the purification part were calculated using a process stimulator (AspenPlus), and the results are shown in Tables 2 and 3 below.

In addition, the amounts of energy used in each of the condensation separation part and the purification part were calculated using a process stimulator (AspenPlus), and the results are shown in Table 4.

Example 2

Except that nitrogen gas was fed so that oxygen concentration in the discharge stream B5 discharged to the incinerator became 6 mol %, butadiene was prepared using the same method as in Example 1.

The amounts of energy used in each of the condensation separation part and the purification part were calculated using a process stimulator (AspenPlus), and the results are shown in Table 4.

Comparative Example 1

To prepare butadiene from butene, the device shown in FIG. 2 was used, raffinate-3 having compositions shown in Table 2 was used as a butene source, and butane was used as a diluent gas. In this case, COx and $O_2$ were recovered, and hydrocarbons were absorbed through compression/cooling and absorption without addition of a noncombustible diluent gas.

In this case, condensation was performed at a pressure of 8 KCG using cooling water having a temperature of 35° C. in the condensation separation part. In the condensation separation part and the purification part, DMF was used as a solvent. When the amount of butadiene was lost by 3.6 kg/hr, the composition of the discharge stream B5 to be incinerated and the amounts of energy used in each of the condensation separation part and the purification part were calculated using a process stimulator (AspenPlus), and the results are shown in Table 4.

Comparative Example 2

To prepare butadiene from butene, the device shown in FIG. 2 was used, and butane was used as a diluent gas. In this case, light gases were recovered through compression/cooling without addition of a noncombustible diluent gas. The C4 fraction was not absorbed, and thus all of noncondensed butadiene was lost. In this case, condensation was performed at a pressure of 8 KCG using cooling water having a temperature of 35° C. in the condensation separation part. In the purification part, DMF was used as a solvent. The composition of the B5 stream to be incinerated and the amounts of energy used in each of the condensation separation part and the purification part were measured, and the results are shown in Table 3.

TABLE 1

| Composition | mol % | % by weight |
|---|---|---|
| 1-Butene | 0.00 | 0.00 |
| Trans-2-butene | 43.20 | 42.77 |
| Cis-2-butene | 28.80 | 28.51 |
| n-Butane | 28.00 | 28.72 |

TABLE 2

| Classification | MW | B1 kg/hr | B1 wt % | B2 kg/hr | B2 wt % | B3 kg/hr | B3 wt % | B4 kg/hr | B4 wt % | B5 kg/hr | B5 wt % |
|---|---|---|---|---|---|---|---|---|---|---|---|
| $N_2$ | 28.0 | 0.0 | 0.0 | 0.0 | 0.0 | 1.6 | 0.2 | 0.0 | 0.0 | 442.8 | 49.6 |
| $CO_2$ | 44.0 | 145.5 | 2.2 | 145.5 | 3.0 | 196.6 | 25.2 | 0.3 | 0.0 | 145.2 | 16.3 |
| CO | 28.0 | 9.3 | 0.1 | 9.3 | 0.2 | 9.4 | 1.2 | 0.0 | 0.0 | 9.3 | 1.0 |
| $O_2$ | 32.0 | 73.8 | 1.1 | 73.8 | 1.5 | 74.6 | 9.6 | 0.0 | 0.0 | 73.8 | 8.3 |
| Butane | 58.1 | 3740.0 | 57.1 | 3740.0 | 78.2 | 401.8 | 51.5 | 3524.2 | 81.4 | 215.8 | 24.2 |
| 1,3-Butadiene | 54.1 | 712.0 | 10.9 | 712.0 | 14.9 | 85.6 | 11.0 | 708.5 | 16.4 | 3.6 | 0.4 |
| Butene | 56.1 | 98.9 | 1.5 | 98.9 | 2.1 | 10.1 | 1.3 | 96.6 | 2.2 | 2.3 | 0.3 |
| HB | 72.1 | 11.3 | 0.2 | 0.0 | 0.0 | 0.0 | 0.0 | 0.0 | 0.0 | 0.0 | 0.0 |
| Water | 18.0 | 1760.6 | 26.9 | 0.0 | 0.0 | 0.0 | 0.0 | 0.0 | 0.0 | 0.0 | 0.0 |
| Sum | | 6551.6 | 100 | 4779.7 | 100 | 779.5 | 100 | 4329.7 | 100 | 892.8 | 100 |

TABLE 3

| Classification | MW | B6 kg/hr | B6 wt % | B7 kg/hr | B7 wt % | B8 kg/hr | B8 wt % | Diluent gas kg/hr | Diluent gas wt % | 1,3-Butadiene kg/hr | 1,3-Butadiene wt % |
|---|---|---|---|---|---|---|---|---|---|---|---|
| $N_2$ | 28.0 | 1.6 | 0.5 | 0.0 | 0.0 | 0.0 | 0.0 | 442.8 | 100 | 0.0 | 0.0 |
| $CO_2$ | 44.0 | 51.4 | 15.6 | 0.0 | 0.0 | 0.0 | 0.0 | 0.0 | 0.0 | 0.0 | 0.0 |
| CO | 28.0 | 0.1 | 0.0 | 0.0 | 0.0 | 0.0 | 0.0 | 0.0 | 0.0 | 0.0 | 0.0 |
| $O_2$ | 32.0 | 0.7 | 0.2 | 0.0 | 0.0 | 0.0 | 0.0 | 0.0 | 0.0 | 0.0 | 0.0 |
| Butane | 58.1 | 186.0 | 56.5 | 3524.2 | 99.5 | 0.0 | 0.0 | 0.0 | 0.0 | 0.0 | 0.0 |
| 1,3-Butadiene | 54.1 | 82.0 | 24.9 | 7.1 | 0.2 | 7.1 | 7.8 | 0.0 | 0.0 | 694.3 | 99.5 |
| Butene | 56.1 | 7.8 | 2.4 | 9.7 | 0.3 | 83.5 | 92.2 | 0.0 | 0.0 | 3.5 | 0.5 |
| HB | 72.1 | 0.0 | 0.0 | 0.0 | 0.0 | 0.0 | 0.0 | 0.0 | 0.0 | 0.0 | 0.0 |
| Water | 18.0 | 0.0 | 0.0 | 0.0 | 0.0 | 0.0 | 0.0 | 0.0 | 0.0 | 0.0 | 0.0 |
| Sum | | 329.5 | 100 | 3541.0 | 100 | 90.5 | 100 | 422.8 | 100 | 697.8 | 100 |

TABLE 4

| Classification | | Example 1 | Example 2 | Comparative Example 1 | Comparative Example 2 |
|---|---|---|---|---|---|
| | | Condensation and adsorption ($N_2$ input) | Condensation and adsorption ($N_2$ input) | Condensation and adsorption | Condensation |
| Condensation temperature | °C. | 35 | 35 | 35 | 35 |
| Loss of butadiene (B5) | kg/hr | 3.6 | 3.6 | 3.6 | 62.3 |
| Input amount of $N_2$ | kg/hr | 443 | 798 | 0 | 0 |
| B5 composition $N_2$ | wt % | 49.6 | 63.2 | 0.0 | 0.0 |
| $CO_2$ | wt % | 16.3 | 11.5 | 31.8 | 25.3 |
| CO | wt % | 1.0 | 0.7 | 2.0 | 1.6 |
| $O_2$ | wt % | 8.3 | 5.9 | 16.1 | 12.9 |
| HC | wt % | 24.8 | 18.7 | 50.1 | 60.2 |

| | | Condensation separation part | Purification part | Condensation separation part | Purification part | Condensation separation part | Purification part | Condensation separation part | Purification part |
|---|---|---|---|---|---|---|---|---|---|
| Steam | Gcal/hr | 0.7 | 2.5 | 1.0 | 3.0 | 0.5 | 2.1 | 0.2 | 1.9 |
| Cooling water | Gcal/hr | 0.9 | 1.0 | 0.9 | 1.1 | 0.9 | 0.9 | 0.5 | 0.7 |
| Refrigerant | Gcal/hr | 0.4 | 0.0 | 0.7 | 0.0 | 0.3 | 0.0 | 0.0 | 0.0 |
| Solvent | ton/hr | 4.7 | 11.8 | 6.6 | 11.8 | 2.2 | 12.2 | 0.0 | 14.4 |
| Electric power | kW | 118.1 | 50.8 | 118.1 | 50.6 | 118.1 | 50.9 | 105.4 | 48.7 |

As shown in Tables 2 to 4, in the case of Example 1 according to the present invention, unlike Comparative Example 1, since nitrogen is fed as a noncombustible diluent gas, the concentrations of each of oxygen and hydrocarbons, which are discharged to the incinerator through the stream B5, are reduced. Thus, the stream is out of an explosive range, thereby securing process stability.

In addition, in the case of Example 2, the amount of nitrogen introduced as a noncombustible diluent gas is increased to further lower oxygen concentration compared to Example 1, thereby further improving process stability. In the case of Comparative Example 2, since hydrocarbons are not absorbed, oxygen concentration is lowered in the stream B5 discharged to the incinerator. Thus, process stability is secured. However, the amount of loss of butadiene is increased.

DESCRIPTION OF SYMBOLS

110, 210, 310, 410, 510, 610: OXIDATIVE DEHYDROGENATION REACTION PART
130, 250, 350, 450, 550, 650: ABSORPTION SEPARATION PART
120, 320, 420, 520, 620: COOLING SEPARATION PART
230, 330, 430, 530, 630: CONDENSATION SEPARATION PART
140, 240, 340, 440, 540, 640: PURIFICATION PART
360, 460, 560, 660: DEGASIFICATION PART
470, 670: HIGH-BOILING POINT MATERIAL REMOVAL PART
531, 631: COMPRESSOR
532, 632: HEAT EXCHANGER

What is claimed is:

1. A method of preparing butadiene, comprising:
   subjecting reaction raw materials containing butene, oxygen ($O_2$), steam, and butane to an oxidative dehydrogenation reaction to produce oxidative dehydrogenation reaction products comprising butadiene, n-butane, butene, oxygen, water and $CO_x$;
   separating water from the oxidative dehydrogenation reaction products by cooling;
   compressing and cooling with a refrigerant the oxidative dehydrogenation reaction products from which water is separated to produce a first stream comprising oxidative dehydrogenation reaction products containing uncondensed hydrocarbons and a second stream comprising crude hydrocarbons including butadiene, n-butane and butene,
   wherein the refrigerant used in the compressing and cooling is one or more selected from the group consisting of: cooling water, ethylene glycol, an aqueous solution of ethylene glycol having a concentration of 20 to 100% by weight, propylene glycol, an aqueous solution of propylene glycol having a concentration of 30 to 100% by weight, and a propylene-based solvent;
   subjecting the first stream to absorption separation under conditions wherein a noncombustible diluent gas is fed, thereby separating COx, $O_2$;
   (i) purifying the second stream to separate butadiene therefrom; or ii) degasifying the second stream to additionally separate COx and $O_2$, and then purifying the second stream to separate butadiene therefrom,
   recycling a gas comprising n-butane remaining after butadiene is separated in the purifying step into the oxidative dehydrogenation reaction in a third stream; and mixing a fourth stream containing butene remaining after butadiene is separated in the purifying step with butene supplied as raw material to the oxidative dehydrogenation reaction.

2. The method according to claim 1, wherein oxygen ($O_2$) contained in the reaction raw materials is fed in a gaseous form having a purity of 90% or more.

3. The method according to claim 1, wherein, in the oxidative dehydrogenation reaction, oxidative dehydrogenation is performed in a molar ratio of butene:oxygen:steam:butane gas of 1:0.5 to 3:0.1 to 20:0.1 to 20.

4. The method according to claim 1, wherein the compressing and cooling is performed by passing the oxidative dehydrogenation reaction products from which water is separated through a condensation separation part having a single-stage compression structure having one stage, a multistage compression structure having 1 to 10 stages, or a multistage compression structure having 1 to 2 stages, and, in the condensation separation part, a compression discharge temperature is 50 to 250° C.

5. The method according to claim 1, wherein the non-combustible diluent gas is nitrogen gas ($N_2$), argon, helium, or carbon dioxide ($CO_2$).

6. The method according to claim 1, further comprising:
feeding COx and $O_2$ additionally separated in the degasification of the second stream to the absorption separation step; and
feeding crude hydrocarbons comprising n-butane, butene, and butadiene excluding COx and $O_2$, which are additionally separated in the degasification step, into the purifying step.

7. The method according to claim 1, further comprising:
feeding COx and $O_2$ additionally separated in the degasification step into the absorption separation step;
removing high-boiling point materials by subjecting crude hydrocarbons comprising n-butane, butene, and butadiene excluding COx and $O_2$, which are additionally separated in the degasification step, through a high-boiling point material removal step; and
purifying crude hydrocarbons, from which the high-boiling point materials are removed.

8. The method according to claim 1, further comprising:
feeding COx and $O_2$, which are additionally separated in the degasification step, to the compressing and cooling step; and
subjecting crude hydrocarbons comprising n-butane, butene, and butadiene excluding COx and $O_2$, which are additionally separated in the degasification step, to the purifying step.

9. The method according to claim 1, further comprising:
subjecting COx and $O_2$, which are additionally separated in the degasification step, to the compressing and cooling step;
removing high-boiling point materials by subjecting crude hydrocarbons comprising n-butane, butene, and butadiene excluding COx and $O_2$, which are additionally separated in the degasification step, to a high-boiling point material removal step;
feeding crude hydrocarbons, from which the high-boiling point materials are removed, to the purifying step.

10. The method according to claim 1, wherein the oxidative dehydrogenation reaction is performed at a reaction temperature of 150 to 650° C. under isothermal or adiabatic conditions, a gas containing butene, oxygen ($O_2$), steam, and n-butane is used as a reaction raw material and a ferrite catalyst is used as a catalyst for the oxidative dehydrogenation reaction, wherein n-butane is a residue remaining after butadiene is separated by the purifying step and is recycled to the oxidative dehydrogenation reaction.

11. The method according to claim 1, wherein the separating water from the oxidative dehydrogenation reaction products by cooling is performed in a cooling separation part in the form of a quenching-type direct cooling system (quencher) or an indirect cooling system.

12. The method according to claim 1, wherein the absorption separation is performed using a solvent capable of selectively absorbing butadiene.

13. The method according to claim 1, wherein the degasification is performed by stripping using a column.

14. The method according to claim 1, wherein the purifying step produces a discharge stream, through which a separated solvent is circulated to the absorption separation step.

* * * * *